United States Patent
Hovis et al.

(10) Patent No.: US 7,678,957 B2
(45) Date of Patent: Mar. 16, 2010

(54) ALKYLATION PROCESS WITH CATALYST TRANSFER

(75) Inventors: Keith W. Hovis, Stillwater, OK (US); Khalid Iqbal, Katy, TX (US); Mark R. Cragun, Bartlesville, OK (US)

(73) Assignee: UOP LLC, Des Plaines, IL (US)

( * ) Notice: Subject to any disclaimer, the term of this patent is extended or adjusted under 35 U.S.C. 154(b) by 1334 days.

(21) Appl. No.: 11/095,835

(22) Filed: Mar. 31, 2005

(65) Prior Publication Data
US 2006/0224033 A1 Oct. 5, 2006

(51) Int. Cl.
*C07C 2/60* (2006.01)
(52) U.S. Cl. .................. 585/723; 585/724; 585/730
(58) Field of Classification Search .............. 585/723, 585/724, 730
See application file for complete search history.

(56) References Cited

U.S. PATENT DOCUMENTS

| | | | |
|---|---|---|---|
| 3,957,902 A | 5/1976 | Mikulicz et al. | 260/683.48 |
| 4,409,420 A | 10/1983 | Van Pool et al. | 585/723 |
| 4,476,097 A | 10/1984 | Van Pool et al. | 422/112 |
| 4,938,935 A | 7/1990 | Audeh et al. | 423/240 |
| 5,021,223 A | 6/1991 | Hovis | 422/198 |
| 5,098,668 A | 3/1992 | Callen et al. | 422/111 |
| 5,146,036 A | 9/1992 | Hovis | 585/723 |

OTHER PUBLICATIONS

Driedger, Walter, "Controlling Vessels and Tanks", P. Eng., Sep. 7, 2001, pp. 1-21 (retrieved from www.driedger.ca/.).*

* cited by examiner

*Primary Examiner*—In Suk Bullock
(74) *Attorney, Agent, or Firm*—James C Paschall

(57) ABSTRACT

A system and/or process for alkylating hydrocarbons which includes an improved method of safely handling alkylation catalyst is disclosed. The process includes passing the alkylation catalyst from a settler vessel to a catalyst receiving vessel, via a catalyst cooler, for containment therein in the presence of a condensible gas. Also disclosed is a method for controlling the pressure in the catalyst receiving vessel by controlling the rate of removal of vapors.

26 Claims, 1 Drawing Sheet

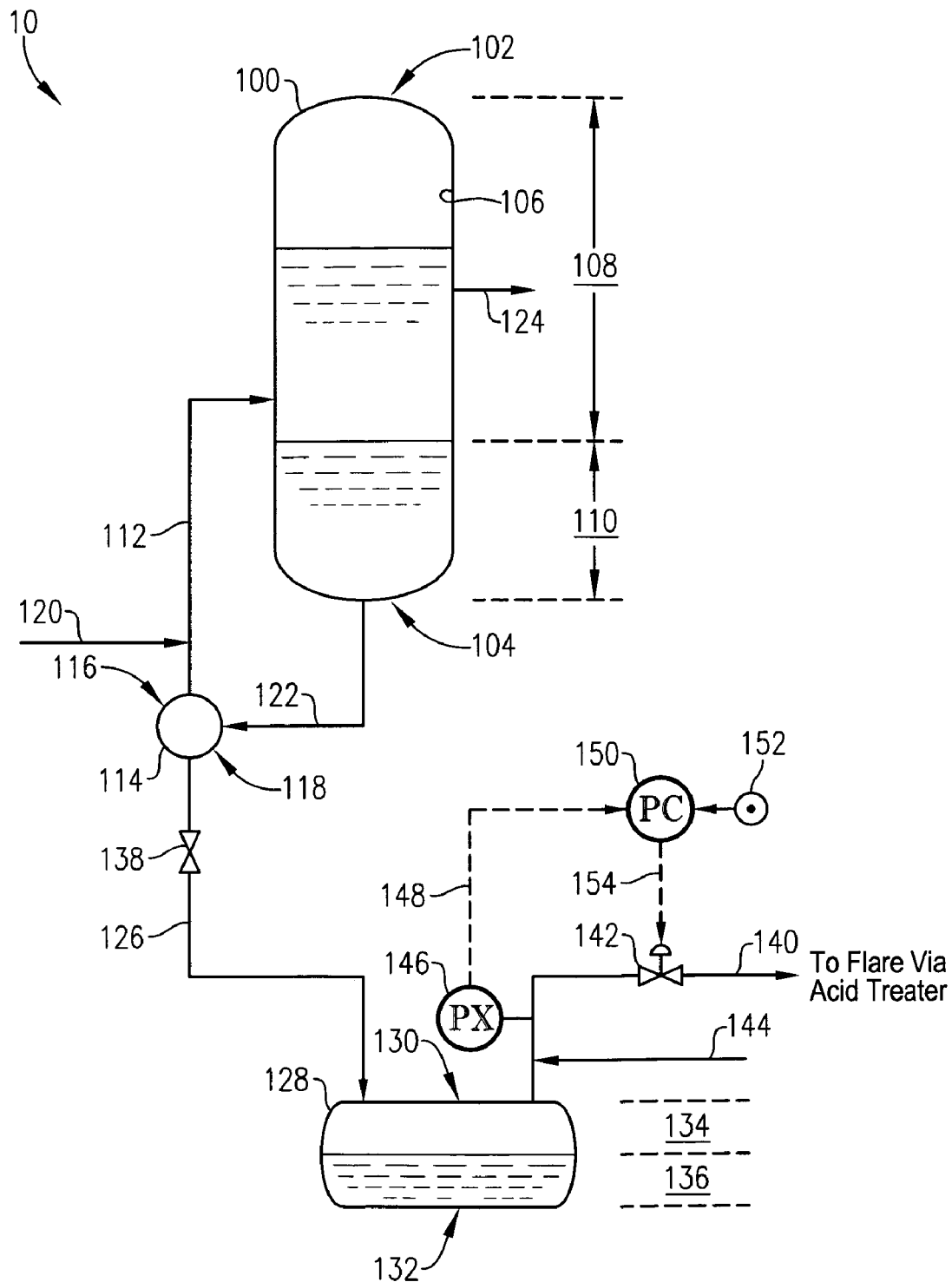

ALKYLATION PROCESS WITH CATALYST TRANSFER

The present invention relates to a process and/or system for the alkylation of an olefin with an isoparaffin utilizing an acidic catalyst mixture. In another aspect, this invention relates to a process and/or system useful for handling fluids in an alkylation process.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the reaction mixture to separate the catalyst from the hydrocarbons, thereby forming a catalyst phase and a hydrocarbon phase. The hydrocarbon phase is further separated, for example, by fractionation, to recover the separate product streams. Normally, the hydrocarbon phase of the alkylation process contains hydrocarbons having three to ten carbon atoms per molecule. In order to have the highest quality gasoline blending stock, it is preferred for the alkylate hydrocarbons formed in the alkylation process to be highly branched and contain seven to nine carbon atoms per molecule.

The safe handling and storage of alkylation catalyst has long been a concern to those operating alkylation units. Refiners have typically employed catalyst receiving vessel(s) located below a settler vessel which is/are suitable for receiving the alkylation catalyst volume contained in the alkylation unit and/or suitable for holding make-up catalyst needed to periodically recharge the alkylation process as catalyst is consumed during operation. These catalyst receiving vessels have typically been operated under a blanket of non-condensible gas such as nitrogen, and non-condensible gases can otherwise enter the catalyst receiving vessel during transfer operations. These catalyst receiving vessels are usually vented to a flare, via a treating system wherein acid is neutralized, during a catalyst transfer from the process unit or during a fresh catalyst receiving operation. Such venting is preferably minimized due to environmental and economical considerations. One problem with the current catalyst receiving vessel system is that as the pressure in the catalyst receiving vessel increases due to the addition of catalyst to the vessel containing non-condensible gas, the motive force for transferring catalyst diminishes. While this is not necessarily detrimental to a fresh catalyst loading operation, it is a significant safety concern for the transfer of catalyst from the process (usually reserved for emergency situations) wherein faster transfer times are preferred.

Therefore, development of an improved process and/or system for transferring alkylation catalyst to a catalyst receiving vessel would be a significant contribution to the art.

BRIEF SUMMARY OF THE INVENTION

It is, thus, an object of the present invention to provide an improved process and/or system for transferring alkylation catalyst to a catalyst receiving vessel.

A further object of this invention is to provide an improved process and/or system for transferring alkylation catalyst to a catalyst receiving vessel using gravitational force and/or pressure differential while minimizing the extent to which vapors in the catalyst receiving vessel are vented.

Another object of this invention is to provide a process and/or system for transferring alkylation catalyst to a catalyst receiving vessel while minimizing the size of the catalyst receiving vessel.

A yet further object of this invention is to provide a process and/or system for the quick transfer of catalyst from an alkylation process.

Other broad objects of this invention are to improve the environmental safety of the alkylation process and to improve the economics of operating an alkylation unit.

In accordance with a first embodiment of the present invention, a system is provided including the following:

a settler vessel comprising a settler vessel top, a settler vessel bottom, an upper zone containing a hydrocarbon phase and a lower zone containing a catalyst phase, wherein the settler vessel bottom is positioned at a first elevation;

a catalyst cooler comprising a catalyst cooler top and a catalyst cooler bottom, wherein the catalyst cooler top is positioned at a second elevation below the first elevation;

a riser reactor connected in fluid flow communication with the catalyst cooler and the upper zone of the settler vessel;

a first conduit connected in fluid flow communication with the riser reactor for introducing a hydrocarbon mixture to the riser reactor for contact with at least a portion of the catalyst phase;

a second conduit connected in fluid flow communication with the lower zone of the settler vessel and the catalyst cooler for transferring the at least a portion of the catalyst phase from the lower zone of the settler vessel to the catalyst cooler;

a third conduit connected in fluid flow communication with the upper zone of the settler vessel for removing at least a portion of the hydrocarbon phase for further processing, wherein the improvement comprises:

providing a catalyst receiving vessel comprising a catalyst receiving vessel top, a catalyst receiving vessel bottom, a pressure, an upper zone and a lower zone, wherein the catalyst receiving vessel top is positioned at a third elevation below the first elevation, and wherein the catalyst receiving vessel is suitable for receiving the catalyst phase and/or the hydrocarbon phase from the settler vessel;

providing a fourth conduit connected in fluid flow communication with the catalyst cooler and the catalyst receiving vessel suitable for transferring fluid from the catalyst cooler to the catalyst receiving vessel with the fourth conduit having interposed therein a valve for blocking passage of fluid through the fourth conduit and, alternately, for allowing passage of fluid through the fourth conduit;

providing a fifth conduit connected in fluid flow communication with the upper zone of the catalyst receiving vessel for adjusting the pressure of the catalyst receiving vessel by removing vapors from the catalyst receiving vessel; and providing a sixth conduit connected in fluid flow communication with the upper zone of the catalyst receiving vessel for introducing a condensible gas into the catalyst receiving vessel to inhibit air from entering the catalyst receiving vessel.

In accordance with a second embodiment of the present invention, a process is provided including the following:

introducing a hydrocarbon mixture comprising at least one olefin and at least one isoparaffin into a riser reactor via a first conduit for contact with an alkylation catalyst within the riser reactor to thereby produce a reactor effluent;

passing the reactor effluent from the riser reactor to a settler vessel comprising a settler vessel top, a settler vessel bottom, wherein the settler vessel bottom is positioned at a first elevation, and wherein the reactor effluent is separated into a hydrocarbon phase and a catalyst phase;

passing at least a portion of the catalyst phase from the settler vessel via a second conduit to a catalyst cooler comprising a catalyst cooler top and a catalyst cooler bottom, wherein the catalyst cooler top is positioned at a second elevation below the first elevation, for cooling, thereby forming a cooled catalyst;

removing at least a portion of the hydrocarbon phase from the settler vessel via a third conduit to thereby form a settler effluent stream;

passing the cooled catalyst from the catalyst cooler to the riser reactor for use as at least a portion of the alkylation catalyst, wherein the improvement comprises:

a) providing a fourth conduit connected in fluid flow communication with the catalyst cooler and a catalyst receiving vessel comprising a catalyst receiving vessel top, a catalyst receiving vessel bottom, a pressure, an upper zone and a lower zone, wherein the catalyst receiving vessel top is positioned at a third elevation below the first elevation, the fourth conduit for transferring the catalyst phase to the catalyst receiving vessel with the fourth conduit having interposed therein a valve for blocking passage of fluid through the fourth conduit and, alternately, for allowing passage of fluid through the fourth conduit;

b) providing a fifth conduit connected in fluid flow communication with the upper zone of the catalyst receiving vessel;

c) providing a sixth conduit connected in fluid flow communication with the upper zone of the catalyst receiving vessel;

d) introducing a condensible gas into the catalyst receiving vessel, through the sixth conduit, to inhibit air from entering the catalyst receiving vessel;

e) opening the valve to thereby allow transfer of the catalyst phase from the settler vessel, through the catalyst cooler and the fourth conduit, to the catalyst receiving vessel by gravitational force and/or pressure differential means; and f) allowing adjustment of the pressure of the catalyst receiving vessel by allowing the removal of vapors from the catalyst receiving vessel through the fifth conduit.

BRIEF DESCRIPTION OF THE DRAWING

The FIGURE is a simplified schematic flow diagram presenting an embodiment of the present invention.

DETAILED DESCRIPTION OF THE INVENTION

The system and process of the present invention will be described with reference to the FIGURE.

Referring to the FIGURE, therein is illustrated the inventive process, system or apparatus 10 including a settler vessel 100 comprising a settler vessel top 102, a settler vessel bottom 104, and an inside wall 106 which defines a settling zone comprising an upper zone 108, and a lower zone 110. Settler vessel bottom 104 is positioned at a first elevation. A riser reactor 112 is connected in fluid flow communication with upper zone 108 of settler vessel 100 and a catalyst cooler 114 comprising a catalyst cooler top 116 and a catalyst cooler bottom 118. Catalyst cooler top 116 is positioned at a second elevation below the first elevation. A hydrocarbon mixture comprising at least one olefin and at least one isoparaffin is introduced into riser reactor 112 via a first conduit 120 connected in fluid flow communication with riser reactor 112 for contact with an alkylation catalyst within riser reactor 112 to thereby produce a reactor effluent. The reactor effluent is passed from riser reactor 112 to upper zone 108 of settler vessel 100 wherein the reactor effluent is separated into a hydrocarbon phase and a catalyst phase.

Upper zone 108 contains the hydrocarbon phase comprising, consisting of, or consisting essentially of unreacted isoparaffins, alkylate product and a component selected from the group consisting of hydrofluoric acid, water, a volatility reducing additive, and combinations of any two or more thereof. Lower zone 110 contains the catalyst phase comprising, consisting of, or consisting essentially of an alkylation catalyst. The alkylation catalyst comprises an acid which can comprise, consist of, or consist essentially of hydrofluoric acid. Optionally, the alkylation catalyst can comprise, consist of, or consist essentially of hydrofluoric acid and a component selected from the group consisting of acid soluble oil, other hydrocarbons, a volatility reducing additive, water and combinations thereof.

The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpyridines, picoline, melamine, hexamethylene-tetramine and the like.

The sulfones suitable for use in this invention are the sulfones of the general formula

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

At least a portion of the catalyst phase can be passed, via a second conduit 122 connected in fluid flow communication with lower zone 110 of settler vessel 100 and catalyst cooler 114, from lower zone 110 of settler vessel 100 to catalyst cooler 114 for cooling, thereby forming a cooled catalyst. At least a portion of the hydrocarbon phase is removed as a settler effluent stream, for further processing, from upper zone 108 of settler vessel 100 via a third conduit 124 connected in fluid flow communication with upper zone 108 of settler vessel 100. At least a portion of the cooled catalyst is passed from catalyst cooler 114 to riser reactor 112 for use as at least a portion of the alkylation catalyst present in riser reactor 112.

The improvement comprising the following.

Providing a fourth conduit 126 connected in fluid flow communication with catalyst cooler 114 and a catalyst receiving vessel 128 comprising a catalyst receiving vessel top 130, a catalyst receiving vessel bottom 132, a pressure, an upper zone 134 and a lower zone 136. Catalyst receiving vessel top 130 is positioned at a third elevation below the first elevation and is suitable for receiving the catalyst phase from settler vessel 100. Preferably, the third elevation is below catalyst cooler bottom 118 and catalyst receiving vessel 128 is also preferably suitable for receiving the hydrocarbon phase from settler vessel 100. Fourth conduit 126 is suitable for transferring the catalyst phase to catalyst receiving vessel 128 and fourth conduit 126 has interposed therein a valve 138 for blocking passage of fluid through fourth conduit 126 and, alternately, for allowing passage of fluid through fourth conduit 126. Valve 138 is positioned at a fourth elevation below the second elevation. In addition, the fourth elevation can be at or above the third elevation, or, alternately, below the third elevation.

A fifth conduit 140 is connected in fluid flow communication with upper zone 134 of catalyst receiving vessel 128 for adjusting the pressure of catalyst receiving vessel 128 by removing vapors from catalyst receiving vessel 128, preferably for venting to a flare via a treating system wherein acid is neutralized.

Fifth conduit 140 preferably has interposed therein a vent valve 142 for blocking passage of fluid through fifth conduit 140 and, alternately, for allowing passage of fluid through fifth conduit 140.

A sixth conduit 144 is connected in fluid flow communication with upper zone 134 of catalyst receiving vessel 128, either directly or via fifth conduit 140, for introducing a condensible gas into catalyst receiving vessel 128 to inhibit air from entering catalyst receiving vessel 128. The use of a condensible gas allows for the use of a catalyst receiving vessel 128 which is smaller than a catalyst receiving vessel which would be necessary without use of a condensible gas.

From time to time as needed, a condensible gas is introduced into catalyst receiving vessel 128, through sixth conduit 144, to inhibit air from entering catalyst receiving vessel 128. The condensible gas is preferably a hydrocarbon gas, is more preferably selected from the group consisting of propane, butane, isobutane, pentane, isopentane, liquefied petroleum gas, and combinations of any two or more thereof, and most preferably comprises isobutane.

At those times when it is desired to remove the catalyst phase from the alkylation system, valve 138 is opened to thereby allow transfer of the catalyst phase from settler vessel 100, through catalyst cooler 114 and fourth conduit 126, to catalyst receiving vessel 128 by gravitational force and/or pressure differential means.

The pressure of catalyst receiving vessel 128 is adjusted by allowing the removal of vapors from catalyst receiving vessel 128 through fifth conduit 140.

As a further embodiment, a pressure transducer 146 is operably related to catalyst receiving vessel 128 which produces a pressure signal 148 representative of the pressure in catalyst receiving vessel 128.

A pressure controller 150 is operably related to pressure transducer 146 and receives pressure signal 148 and an operator entered pressure signal 152, which is representative of the desired value for the pressure in catalyst receiving vessel 128, wherein pressure controller 150 establishes a pressure control signal 154, responsive to pressure signal 148 and the operator entered pressure signal 152, representative of the flow rate required to maintain the pressure in the catalyst receiving vessel 128, represented by pressure signal 148, substantially equal to the desired value for the pressure of the catalyst receiving vessel 128, represented by operator entered pressure signal 152.

The vent valve 142 is operably related to pressure controller 150 and vent valve 142 is preferably a control valve suitable for adjusting the flow rate of the material carried in fifth conduit 140 in response to pressure control signal 154.

The pressure adjustment of catalyst receiving vessel 128 is preferably performed in the following manner. The pressure in catalyst receiving vessel 128 is measured via pressure transducer 146 producing pressure signal 148.

Pressure signal 148 and operator entered signal 152 are introduced to pressure controller 150.

Pressure control signal 154 is established via the pressure controller 150 and pressure control signal 154 is introduced to vent valve 142.

The flow rate of the material carried in fifth conduit 140 is adjusted via vent valve 142 in response to pressure control signal 154.

Whereas this invention has been described in terms of the preferred embodiments, reasonable variations and modifications are possible by those skilled in the art. Such modifications are within the scope of the described invention and appended claims.

That which is claimed:

1. In an alkylation process including:
   introducing a hydrocarbon mixture comprising at least one olefin and at least one isoparaffin into a riser reactor via a first conduit for contact with an alkylation catalyst within said riser reactor to thereby produce a reactor effluent;
   passing said reactor effluent from said riser reactor to a settler vessel comprising a settler vessel top, a settler vessel bottom, wherein said settler vessel bottom is positioned at a first elevation, and wherein said reactor effluent is separated into a hydrocarbon phase and a catalyst phase;
   passing at least a portion of said catalyst phase from said settler vessel via a second conduit to a catalyst cooler comprising a catalyst cooler top and a catalyst cooler bottom, wherein said catalyst cooler top is positioned at a second elevation below said first elevation, for cooling, thereby forming a cooled catalyst;
   removing at least a portion of said hydrocarbon phase from said settler vessel via a third conduit to thereby form a settler effluent stream;
   passing said cooled catalyst from said catalyst cooler to said riser reactor for use as at least a portion of said alkylation catalyst, wherein the improvement comprises:
   a) providing a fourth conduit connected in fluid flow communication with said catalyst cooler and a catalyst receiving vessel comprising a catalyst receiving vessel top, a catalyst receiving vessel bottom, a pressure, an upper zone and a lower zone, wherein said catalyst receiving vessel top is positioned at a third elevation below said first elevation, said fourth conduit for transferring said catalyst phase to said catalyst receiving vessel with said fourth conduit having interposed therein a valve for blocking passage of fluid through said fourth conduit and, alternately, for allowing passage of fluid through said fourth conduit;
   b) providing a fifth conduit connected in fluid flow communication with said upper zone of said catalyst receiving vessel;
   c) providing a sixth conduit connected in fluid flow communication with said upper zone of said catalyst receiving vessel;
   d) introducing a condensible gas into said catalyst receiving vessel, through said sixth conduit, to inhibit air from entering said catalyst receiving vessel;

e) opening said valve to thereby allow transfer of said catalyst phase from said settler vessel, through said catalyst cooler and said fourth conduit, to said catalyst receiving vessel by gravitational force and/or pressure differential means; and f) allowing adjustment of said pressure of said catalyst receiving vessel by allowing the removal of vapors from said catalyst receiving vessel through said fifth conduit.

2. A process in accordance with claim 1 wherein said valve is positioned at a fourth elevation below said second elevation.

3. A process in accordance with claim 2 wherein said fourth elevation is at or above said third elevation.

4. A process in accordance with claim 2 wherein said fourth elevation is below said third elevation.

5. A process in accordance with claim 1 wherein said fifth conduit has interposed therein a vent valve for blocking passage of fluid through said fifth conduit and, alternately, for allowing passage of fluid through said fifth conduit.

6. A process in accordance with claim 5 further comprising:

providing a pressure transducer operably related to said catalyst receiving vessel which produces a pressure signal representative of the pressure in said catalyst receiving vessel;

providing a pressure controller operably related to said pressure transducer which receives said pressure signal and an operator entered pressure signal, which is representative of the desired value for said pressure in said catalyst receiving vessel, wherein said pressure controller establishes a pressure control signal, responsive to said pressure signal and said operator entered pressure signal, representative of the flow rate required to maintain said pressure in said catalyst receiving vessel, represented by said pressure signal, substantially equal to the desired value for said pressure of said catalyst receiving vessel, represented by said operator entered pressure signal;

wherein said vent valve is operably related to said pressure controller and wherein said vent valve is a control valve suitable for adjusting the flow rate of the material carried in said fifth conduit in response to said pressure control signal;

wherein said step f) is further defined to include:

measuring said pressure in said catalyst receiving vessel via said pressure transducer producing said pressure signal;

introducing said pressure signal and said operator entered signal to said pressure controller;

establishing said pressure control signal via said pressure controller and introducing said pressure control signal to said vent valve;

and adjusting the flow rate of the material carried in said fifth conduit via said vent valve in response to said pressure control signal.

7. A process in accordance with claim 1 wherein said condensible gas is a hydrocarbon gas.

8. A process in accordance with claim 1 wherein said condensible gas is selected from the group consisting of propane, butane, isobutane, pentane, isopentane, liquefied petroleum gas, and combinations of any two or more thereof.

9. A process in accordance with claim 1 wherein said condensible gas comprises isobutane.

10. A process in accordance with claim 1 wherein said alkylation catalyst comprises hydrofluoric acid.

11. A process in accordance with claim 1 wherein said alkylation catalyst comprises hydrofluoric acid and a component selected from the group consisting of acid soluble oil, other hydrocarbons, a volatility reducing additive, water and combinations thereof.

12. A process in accordance with claim 11 wherein said volatility reducing additive is a sulfone.

13. A process in accordance with claim 1 wherein step e) further comprises transfer of said hydrocarbon phase from said settler vessel, through said catalyst cooler and said fourth conduit, to said catalyst receiving vessel by gravitational force and/or pressure differential means.

14. In an alkylation process including:

introducing a hydrocarbon mixture comprising at least one olefin and at least one isoparaffin into a riser reactor via a first conduit for contact with an alkylation catalyst within said riser reactor to thereby produce a reactor effluent;

passing said reactor effluent from said riser reactor to a settler vessel comprising a settler vessel top, a settler vessel bottom, wherein said settler vessel bottom is positioned at a first elevation, and wherein said reactor effluent is separated into a hydrocarbon phase and a catalyst phase;

passing at least a portion of said catalyst phase from said settler vessel via a second conduit to a catalyst cooler comprising a catalyst cooler top and a catalyst cooler bottom, wherein said catalyst cooler top is positioned at a second elevation below said first elevation, for cooling, thereby forming a cooled catalyst;

removing at least a portion of said hydrocarbon phase from said settler vessel via a third conduit to thereby form a settler effluent stream;

passing said cooled catalyst from said catalyst cooler to said riser reactor for use as at least a portion of said alkylation catalyst, wherein the improvement comprises:

a) providing a fourth conduit connected in fluid flow communication with said catalyst cooler and a catalyst receiving vessel comprising a catalyst receiving vessel top, a catalyst receiving vessel bottom, a pressure, an upper zone and a lower zone, wherein said catalyst receiving vessel top is positioned at a third elevation below said first elevation, said fourth conduit for transferring said catalyst phase to said catalyst receiving vessel with said fourth conduit having interposed therein a valve for blocking passage of fluid through said fourth conduit and, alternately, for allowing passage of fluid through said fourth conduit;

b) providing a fifth conduit connected in fluid flow communication with said upper zone of said catalyst receiving vessel;

c) providing a sixth conduit connected in fluid flow communication with said upper zone of said catalyst receiving vessel;

d) introducing a condensible gas into said catalyst receiving vessel, through said sixth conduit, to inhibit air from entering said catalyst receiving vessel;

e) opening said valve to thereby allow transfer of said catalyst phase from said settler vessel, through said catalyst cooler and said fourth conduit, to said catalyst receiving vessel by gravitational force and pressure differential means; and f) allowing adjustment of said pressure of said catalyst receiving vessel by allowing the removal of vapors from said catalyst receiving vessel through said fifth conduit.

15. A process in accordance with claim 14 wherein said valve is positioned at a fourth elevation below said second elevation.

16. A process in accordance with claim 15 wherein said fourth elevation is at or above said third elevation.

17. A process in accordance with claim 15 wherein said fourth elevation is below said third elevation.

18. A process in accordance with claim 14 wherein said fifth conduit has interposed therein a vent valve for blocking passage of fluid through said fifth conduit and, alternately, for allowing passage of fluid through said fifth conduit.

19. A process in accordance with claim 18 further comprising:
  providing a pressure transducer operably related to said catalyst receiving vessel which produces a pressure signal representative of the pressure in said catalyst receiving vessel;
  providing a pressure controller operably related to said pressure transducer which receives said pressure signal and an operator entered pressure signal, which is representative of the desired value for said pressure in said catalyst receiving vessel, wherein said pressure controller establishes a pressure control signal, responsive to said pressure signal and said operator entered pressure signal, representative of the flow rate required to maintain said pressure in said catalyst receiving vessel, represented by said pressure signal, substantially equal to the desired value for said pressure of said catalyst receiving vessel, represented by said operator entered pressure signal;
  wherein said vent valve is operably related to said pressure controller and wherein said vent valve is a control valve suitable for adjusting the flow rate of the material carried in said fifth conduit in response to said pressure control signal;

wherein said step f) is further defined to include:
  measuring said pressure in said catalyst receiving vessel via said pressure transducer producing said pressure signal;
  introducing said pressure signal and said operator entered signal to said pressure controller;
  establishing said pressure control signal via said pressure controller and introducing said pressure control signal to said vent valve;
  and adjusting the flow rate of the material carried in said fifth conduit via said vent valve in response to said pressure control signal.

20. A process in accordance with claim 14 wherein said condensible gas is a hydrocarbon gas.

21. A process in accordance with claim 14 wherein said condensible gas is selected from the group consisting of propane, butane, isobutane, pentane, isopentane, liquefied petroleum gas, and combinations of any two or more thereof.

22. A process in accordance with claim 14 wherein said condensible gas comprises isobutane.

23. A process in accordance with claim 14 wherein said alkylation catalyst comprises hydrofluoric acid.

24. A process in accordance with claim 14 wherein said alkylation catalyst comprises hydrofluoric acid and a component selected from the group consisting of acid soluble oil, other hydrocarbons, a volatility reducing additive, water and combinations thereof.

25. A process in accordance with claim 24 wherein said volatility reducing additive is a sulfone.

26. A process in accordance with claim 14 wherein step e) further comprises transfer of said hydrocarbon phase from said settler vessel, through said catalyst cooler and said fourth conduit, to said catalyst receiving vessel by gravitational force and/or pressure differential means.

* * * * *